United States Patent [19]

Chen

[11] Patent Number: 4,787,403
[45] Date of Patent: Nov. 29, 1988

[54] DENTAL FLOSS HOLDER

[76] Inventor: Kuo-Chun Chen, 1775 Hammond Ct., Bloomfield Hills, Mich. 48013

[21] Appl. No.: 52,992

[22] Filed: Jul. 2, 1987

Related U.S. Application Data

[63] Continuation-in-part of Ser. No. 10,402, Feb. 3, 1987.

[51] Int. Cl.⁴ .............................................. A61C 15/00
[52] U.S. Cl. ..................................................... 132/327
[58] Field of Search .............. 132/91, 92 A, 89, 92 R; 433/141

[56] References Cited

U.S. PATENT DOCUMENTS

| 867,264 | 10/1907 | Evans | 132/92 R |
| 1,952,358 | 3/1934 | Bohm | 132/92 R |
| 1,990,404 | 2/1935 | Doner | 132/92 R |
| 2,467,221 | 4/1949 | Postl | 132/92 R |

Primary Examiner—Robert Peshock
Attorney, Agent, or Firm—Krass & Young

[57] ABSTRACT

A dental floss holder and applicator of the type having an elongated handle and a pair of acutely angled tines projecting from one end of the handle incorporates a screw mechanism for securing the ends of a length of floss to the handle so that the length may be arrayed between the tines. The mechanism includes a screw which passes through a threaded hole at the base of the tines and has heads formed on its opposed ends to allow adjustment of position of the heads with respect to the base so that the ends of the length of floss may be captured between the heads and the base. A portion of the device is marked with color in contrast to the balance of the device to aid in identification of a specific device.

8 Claims, 2 Drawing Sheets

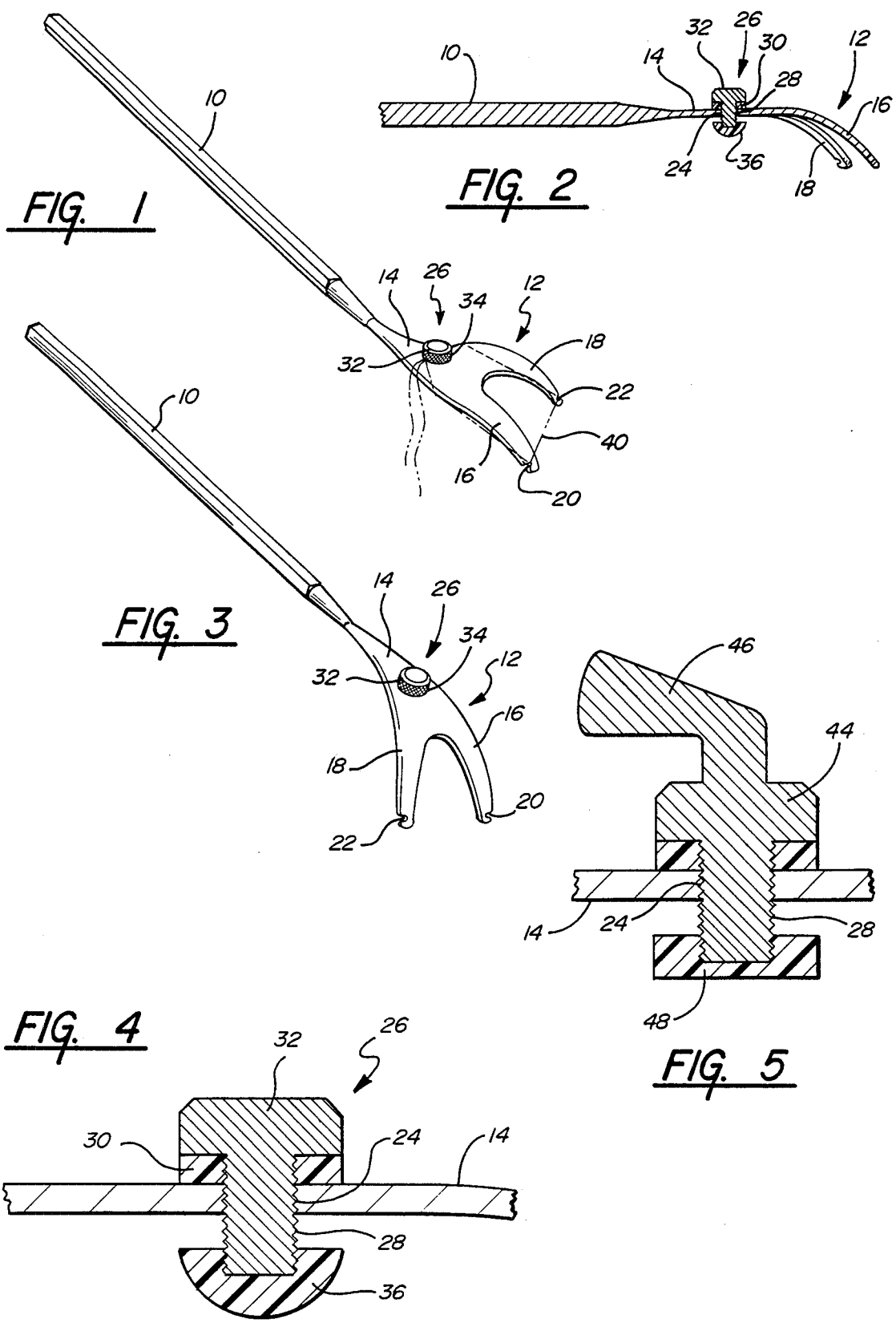

DENTAL FLOSS HOLDER

CROSS-REFERENCE TO RELATED APPLICATION

This application is a continuation-in-part of U.S. application Ser. No. 010,402, filed Feb. 3, 1987, now pending.

BACKGROUND OF THE INVENTION

1. Field of the Invention

This invention relates to a dental floss holder and applicator operative to support a taut section of dental floss and to allow users manual manipulation of the section to clean spaces between the teeth, where decay and many gum diseases originate.

2. Brief Description of the Prior Art

Regular application of dental floss to the spaces between teeth is an important aspect of oral hygiene. The difficulty of holding a section of dental floss between the hands and manipulating it to clean the spaces between all the teeth has motivated the invention of a variety of dental floss holders which support a short section of floss in bridging relation between a pair of spaced tines and allow the manipulation of the short section with a handle member. Previous U.S. patents employing this basic configuration include Nos. 3,672,377; 3,834,404; 3,908,677; and 4,041,962. These patents all disclose dental floss holders having posts secured to a common base of the tines for retaining the free ends of a section of dental floss bridging the tines. The tines are formed with notches at their free ends and a section of floss is extended from the post, through one of the notches, over to the other notch and back to the post. The anchoring posts have been the subject of extensive development and a number of floss holders have employed resilient rings beneath the post for the purposes of capturing the ends of a floss section and elimating the need to repeatedly wrap the end of the floss around the post.

Despite the extensive experimentation with floss holders as evidenced by the large number of issued patents on the devices, none of the holders have attained a high degree of commercial acceptance, and despite the relatively low cost of the holders, floss is still generally applied by the user stretching a section between the hands. It is accordingly an object of the present invention to provide a floss holder that simplifies the floss applying operation to make use of the holder a desirable alternative to manual application of floss.

SUMMARY OF THE INVENTION

The present invention is directed toward improvements in the type of floss holder having a pair of diverging tines projecting from one end of an elongated handle. The present invention provides a floss-retaining post in the form of a short screw mating within a threaded hole formed through the base of the tine section. The screw has a serrated thumbwheel formed at one of its ends and a cap of larger diameter than the screw formed at the other end to prevent removal of the screw from its retaining hole. The screw has sufficient length that it may be rotated between an open position in which the bottom of the thumbwheel is separated from the base of the tines so that floss may be wrapped under the thumbwheel, and a locked position wherein the thumbwheel is rotated to bring its undersurface in engagement with the base of the tines and lock the ends of a floss section which extend beneath the thumbwheel. This screw arrangement provides a simple and convenient method for effectively securing the ends of a length of floss to the holder.

A resilient plastic insert is preferably formed on the underside of the screw wheel to reinforce engagement of the floss section and securely retain it against the tine base. The cap on the opposite side of the screw from the thumbwheel is preferably also formed of either stainless steel, or plastic and may be color coded so that various family members who use the floss applicators can distinguish their personal applicators from one another.

Another aspect of the present invention consists of a tine orientation that allows floss application in a simple and effective manner. Rather than orienting the tines symmetrically about the ends of the handle, as did the applicators of the prior art, in the present invention one of the tines is oriented as a general extension of the axis of the handle and the other tine projects at an acute axis to the handle. Both tines are curved away from the handle in a direction normal to their common plane. This tine orientation allows for easy insertion of the floss in all of the tooth interstices. The arrangement is asymmetrical so that two floss holders of opposite configuration are required for use on opposite sides of the mouth. This embodiment of the invention is intended for use in dental offices, but it is equally suitable to be employed by general population as well.

BRIEF DESCRIPTION OF THE DRAWINGS

Other objectives, advantages, and applications of the present invention will be made apparent by the following detailed description of the preferred embodiment and alternative embodiments of the invention. The description makes reference to the accompaning drawings in which:

FIG. 1 is a perspective view of a dental floss holder forming a preferred embodiment of the invention;

FIG. 2 is a side sectional view through the floss holder of FIG. 1;

FIG. 3 is a perspective view of the preferred embodiment of my invention in a design of opposite hand, intended for use on the opposite side of the mouth with respect to the embodiment of FIG. 1;

FIG. 4 is a detailed sectional view through the floss-retaining screw of the embodiment of FIGS. 1 and 3; and FIG. 5 is a detailed sectional view through an alternative floss-holding screw arrangement.

DETAILED DESCRIPTION OF THE PREFERRED EMBODIMENT

Figure 6:
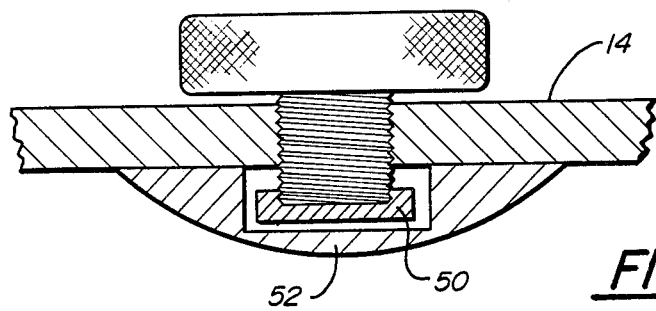
FIGS. 6, 7, & 8 are detailed sectional views through alternative floss-holding screw arrangements.

Referring to the drawings, the floss holders of the present invention are formed of a rigid material. A rigid plastic or plastic and metal in combination is preferable for the consumer version of the device while stainless steel would be more suitable for a professional model intended for use in dental offices.

The floss holders employ an elongated handle 10 which may be flat, cylindrical or hexagonal in cross section. A tine arrangement, generally indicated at 12, is fixed to and projects from one end of the handle 10. The tines are preferably flat in cross section and consist of a base section 14, secured to the end of the handle 10, and a pair of projecting tines 16 and 18. The tines have a length of approximately 1½–3 inches. In one plane through the handle, the tine 16 extends more or less as a projection of the axis of the handle 10 while the tine 18 projects laterally at an angle of about 45 degrees to the tine 16 and to the axis of the handle. In a second plane, normal to that first plane, the tines are curved away from the handle so that their ends project at approximately 45 degrees to the axis of the handle.

A pair of notches 20 and 22 are formed on the opposed outer sides of the tines 16 and 18 adjacent their free ends. The notches act as retaining sections for a length of floss.

A threaded hole 24 is formed through the base 14 of the tines, and a screw anchoring post, generally indicated at 26, is retained within the threaded hole. The anchoring post includes a screw section 28, illustrated in detail in FIGS. 4 or 5, which has a length of about twice the thickness of the tine base. The upper end of the screw 28 is fixed within a plastic insert 30 formed centrally within the underside of a metal thumbscrew 32. The thumbscrew 32 has serrations 34 on its outer perimeter to allow it to be easily rotated. The other end of the screw 28 is fixed within a semi-spherical stainless steel or plastic end cap 36. The distance between the opposed surfaces of the insert 30 and the cap 36 allow screw 28 to be rotated to move the thumbwheel 32 toward and away from the surface of the tine base.

In use, with the post in the unlocked position, one end of a length of floss 40 is wrapped under the thumbwheel 32, carried through the notch 20 and over to the notch 22 in the opposite tine and back under the thumbwheel. The thumbwheel is then rotated to lock the ends of the section against the tine base and the floss holder is ready for use. After use, the thumbwheel is loosened and the floss section is removed and discarded.

The orientation of the floss holder illustrated in FIG. 1 makes it suitable for use by a right-handed person to clean the left side of teeth or for use by a left-handed dental technician to clean the right side of a patient's teeth. The floss holder 42, generally illustrated in FIG. 3, has the opposite orientation. It can be used by a left-handed user or right-handed technician. Alternative embodiments of the floss could be formed with the tines projecting symmetrically about the handle so that only a single floss holder is required for use in the mouth.

FIG. 5 illustrated an alternative form of the floss securing arrangement, generally indicated at 42. In this embodiment, the thumbwheel 44 is formed with an upwardly projecting handle member 46. The retaining section 48 on the opposite end of the screw is formed as a stainless steel or plastic disk.

FIG. 6 illustrates an alternative form of the floss securing arrangement. In this form, the retaining section 50 on the opposite end of the screw is formed as a stainless steel or plastic disk. The retaining section 50 is surrounded by a smooth surfaced, dome-like cover 52, preferably formed of plastic or stainless steel. This cover prevents foreign particles from becoming engaged in the crevices of the screw device, thereby facilitating the cleaning of the device.

Figure 7:
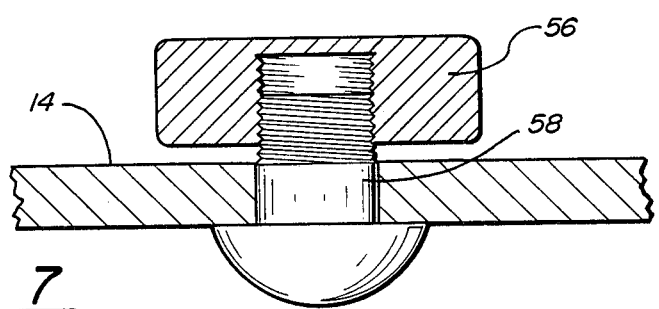

FIG. 7 illustrates another form of the floss securing arrangement. In this embodiment a threaded post 58 is secured in the base 14 of the tines. The thumbwheel 56, which can be in any of the previously described forms, moves up and down on the anchored post 58 as it is manually rotated. This is in contrast to the other embodiments, which consist of a thumbwheel firmly attached to a screw (post) which rotates within a threaded hole.

Figure 8:
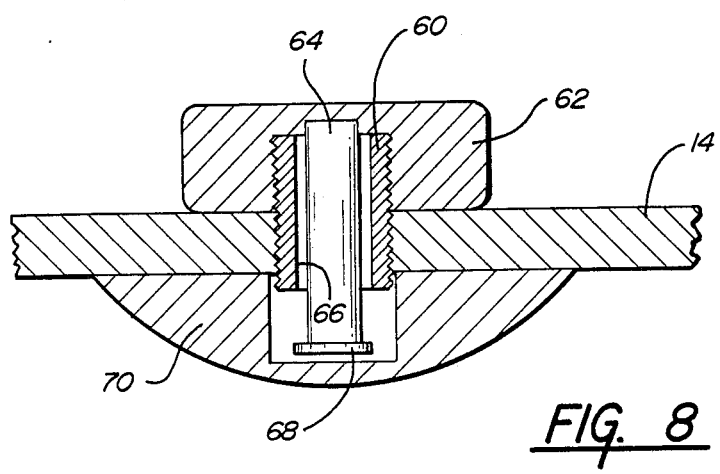

FIG. 8 illustrates yet another alternative form of the floss securing arrangement. In this embodiment a hollow threaded post 60 is secured firmly in the base 14 of the tines. When rotated, the thumbwheel 62 moves up or down the stationary post 60. A rod 64, made of a rigid material, projects downwardly from the center of the thumbwheel 62 and through the hollow portion, generally indicated by 66, of the post 60. The rod 64 projects out of the bottom end of the post 60, past the surface of the base 14 of the tines. The rod 64 is firmly attached to the thumbwheel 62. The bottom end of the rod 64 is made to be wider then the hollow portion 66 of the post 60. This acts as a retaining section, indicated by 68, to prevent the thumbwheel from being removed. This retaining section is covered by a cover 70 similar to that of 52 shown in FIG. 6.

Having thus described my invention, I claim:

1. In a device for supporting a strand of dental floss under tension and allowing manipulation of the floss for use in cleaning teeth, of the type comprising an elongated handle member having a pair of relatively short tines extending from a common base rigidly connected to one end of the handle and diverging outwardly from the handle at an acute angle relative to one another to form free ends, and notches formed on outer sides of the tines adjacent to their free ends for supporting the strand of dental floss tautly between the tines, the improvement comprising:

threaded fastener means engaged with said base including a serrated thumbscrew and being rotatably supported with respect to said base for movement between an unlocked position wherein said thumbscrew is spaced from a surface of the base, and a locked position wherein said thumbscrew is in registry with the surface of the base to lock the strand of dental floss between said thumbscrew and said base, said fastener means including means forming a threaded hole extending through the base in a direction transverse to a longitudinal axis of the handle and a threaded post having two ends, said thumbscrew being disposed at a first of said ends and a head being disposed at a second of said ends, said post being rotatingly engageable with said hole, such that one of the head and the thumbscrew is in registry with the base and the other of the head and the thumbscrew is spaced from the base.

2. The device of claim 1 wherein at least a portion of the device is colored in contrast to the balance of the device to allow identification of the device.

3. The device of claim 2 wherein said head is formed of plastic and constitutes said contrast colored portion.

4. The device of claim 1 including a dome-like cover attached to said base and covering the head of said fastener.

5. The device of claim 1 where said threaded fastener means comprises a tubular, threaded post fixed to the base on which post said thumbscrew is engaged, said thumbscrew being rotatable with respect to said post, a rod attached to said thumbscrew which projects though said tubular post and a retaining means formed on a projecting end of the post to prevent said thumbscrew from being removed from said base.

6. The device of claim 5 including a dome-like cover attached to said common tine base and covering the retaining means.

7. A dental floss holder comprising:

a straight elongated handle;

a pair of flat tines fixed to one end of the handle, the tines extending outwardly from the handle in an acute diverging relationship to one another from a base section joined to one end of the handle, the base section lying in a plane passing through the axis of the handle and the tines being bent outwardly from that plane at an angle that increases as the distance from the base section increases to form free ends which project at approximately a 45 degree angle relative to the base section;

notches formed on outer sides of the opposed tines adjacent their free ends for retention of a length of dental floss;

a threaded hole formed through the base section and transverse to the plane thereof;

a threaded fastener disposed with the hole;

head members formed at opposed ends of the fastener to allow the fastener to be rotated so that one of the heads is in engagement with the base section of the tines and the other head is spaced from the tines; and a resilient insert disposed on one of the head and the thumbscrew on a surface thereof that registers with the tine base, whereby the threaded fastener may be used to secure a section of dental floss to the device.

8. The device of claim 7 including a portion of the device colored in contrast to the balance of the device to aid in identification of a specific device.

* * * * *